United States Patent [19]

Tominaga et al.

[11] Patent Number: 4,760,064
[45] Date of Patent: Jul. 26, 1988

[54] CARBOSTYRIL COMPOUNDS, COMPOSITIONS CONTAINING SAME AND PROCESSES FOR PREPARING SAME

[75] Inventors: Michiaki Tominaga; Takafumi Fujioka; Kazuyoshi Nagami; Kazuyuki Nakagawa, all of Tokushima, Japan

[73] Assignee: Otsuka Pharmaceutical Co., Ltd., Tokyo, Japan

[21] Appl. No.: 808,420

[22] Filed: Dec. 13, 1985

[30] Foreign Application Priority Data

Dec. 18, 1984 [JP] Japan .................................. 59-268189
Dec. 3, 1985 [JP] Japan .................................. 60-272086

[51] Int. Cl.$^4$ .................. A61K 31/495; C07D 401/04
[52] U.S. Cl. ...................................... 514/253; 544/363
[58] Field of Search .......................... 544/363; 514/253

[56] References Cited

U.S. PATENT DOCUMENTS 4,415,572  11/1983  Tominaga et al. .................. 544/363

OTHER PUBLICATIONS

McElvain, *The Characterization of Organic Compounds*, Rev. ed., 1953, MacMillan Co., N.Y., pp. 44–47 and 72–75.
Tominaga et al., "Chem. Pharm. Bull.", vol. 32(6), 1984, pp. 2100–2110.
Yang et al., "Chemical Abstracts", vol. 97, 1982, col. 97:72386f.
"Chemical Abstracts", vol. 99, 1983, col. 99:93742a and col. 99:15827y.
Tominaga et al., "Chemical Abstracts", vol. 102, 1985, col. 102:24584u.

*Primary Examiner*—Glennon H. Hollrah
*Assistant Examiner*—James H. Turnipseed
*Attorney, Agent, or Firm*—Sughrue, Mion, Zinn, Macpeak, and Seas

[57] ABSTRACT

A carbostyril compound of the formula (I):

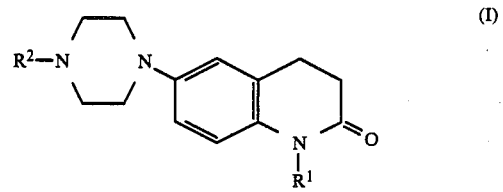

wherein $R^1$ and $R^2$ are as defined or its pharmaceutically acceptable salt, composition containing the compound and processes for preparing the same are disclosed.

The compound is useful as a cardiotonic agent.

20 Claims, No Drawings

CARBOSTYRIL COMPOUNDS, COMPOSITIONS CONTAINING SAME AND PROCESSES FOR PREPARING SAME

BACKGROUND OF THE INVENTION

This invention relates to certain carbostyril compounds and to pharmaceutically acceptable salts thereof which are useful as cardiotonic agents, processes for preparing the same, and pharmaceutical compositions containing the carbostyril compounds or salts thereof.

Various carbostyril compounds are known which have cardiotonic activity as described in U.S. Pat. No. 4,415,572.

However, the carbostyril compounds of this invention are structurally different from the conventional carbostyril compounds.

SUMMARY OF THE INVENTION

One object of this invention is to provide carbostyril compounds having a cardiotonic activity.

Another object of this invention is to provide a pharmaceutical composition containing the carbostyril compound in a cardiotonically effective amount.

A further object of this invention is to provide a process for preparing the carbostyril compounds and pharmaceutically acceptable salts thereof.

As a result of extensive research this invention has been accomplished which, in one aspect, provides a carbostyril compound of the formula (I)

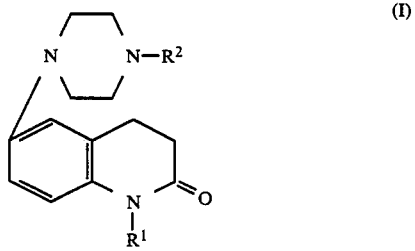

wherein $R^1$ is a lower alkanoyl group, a lower alkoxycarbonyl group, a lower alkoxycarbonyl-lower alkyl group, a phenyl-lower alkyl group which has, on the phenyl ring thereof, at least one substituent selected from among lower alkanoyloxy and hydroxy groups, a benzoyl group which may optionally be substituted, on the phenyl ring thereof, with at least one substituent selected from the group consisting of nitro, unsubstituted or lower alkyl-substituted amino, phenyl-lower alkoxy, hydroxy, carboxy, phenyl-lower alkoxycarbonyl-lower alkoxy, lower alkanoyloxy, carboxy-lower alkoxy, and lower alkyl-substituted amino-lower alkyl, or a naphthoyl group, $R^2$ is a benzoyl group which may optionally have, on the phenyl ring thereof, at least one lower alkoxy group, and a pharmaceutically acceptable salt thereof.

In another aspect, this invention provides a cardiotonic composition containing a compound of the formula (I) or a pharmaceutically acceptable salt thereof in a cardiotonically effective amount.

In a further aspect, this invention provides a process for preparing the compounds of the formula (I) and pharmaceutically acceptable salts thereof.

The carbostyril derivatives of the formula (I) of this invention have a myocardial contractility-increasing activity (positive inotropic effect) and are useful as a cardiotonic agent for treating heart diseases such as congestive heart failure and the like. In addition to the above activity, these compounds advantageously have a coronary blood flow increasing activity, but do not or only slightly, if any, increase heart beats. Furthermore, they have long duration.

DETAILED DESCRIPTION OF THE INVENTION

The term "lower alkanoyl" as used herein refers to straight or branched chain alkanoyl groups of 1 to 6 carbon atoms such as a formyl group, an acetyl group, a propionyl group, a butyryl group, a pentanoyl group, a hexanoyl group and the like.

The term "lower alkoxycarbonyl" as used herein refers to straight or branched chain alkoxycarbonyl groups of 1 to 6 carbon atoms such as a methoxycarbonyl group, an ethoxycarbonyl group, an isopropoxycarbonyl group, a n-butoxycarbonyl group, a tert-butoxycarbonyl group, a pentyloxycarbonyl group, a hexyloxycarbonyl group and the like.

The term "lower alkoxycarbonyl-lower alkyl" as used herein refers to alkoxycarbonylalkyl groups whose alkoxy moiety is a straight or branched chain alkoxy group of 1 to 6 carbon atoms and whose alkyl moiety is a straight or branched chain alkyl group of 1 to 6 carbon atoms. As examples there may be mentioned a methoxycarbonylmethyl group, a 3-methoxycarbonylpropyl group, a 4-ethoxycarbonylbutyl group, a 6-propoxycarbonylhexyl group, a 5-isopropoxycarbonylpentyl group, a 1,1-dimethyl-2-butoxycarbonylethyl group, a 2-methyl-3-tert-butoxycarbonylpropyl group, a 2-pentyloxycarbonylethyl group, a 2-hexyloxycarbonylethyl group and the like.

The term "phenyl-lower alkyl group which has, on the phenyl ring thereof, at least one substituent selected from among lower alkanoyloxy and hydroxy groups" as used herein refers to phenyl alkyl groups having, as substituents on the phenyl ring thereof, 1 to 3 straight or branched chain alkanoyloxy groups of 1 to 6 carbon atoms and/or hydroxy groups, and the alkyl moiety being a straight or branched chain alkyl group of 1 to 6 carbon atoms. As examples there may be mentioned a 2-, 3- or 4-hydroxybenzyl group, a 2-(3,4-dihydroxyphenyl)ethyl group, a 1-(3,4-dihydroxyphenyl)ethyl group, a 2-(3-hydroxyphenyl)ethyl group, a 3-(4-hydroxyphenyl)propyl group, a 6-(3,4-dihydroxyphenyl)hexyl group, a 3,4-dihydroxybenzyl group, a 3,4,5-trihydroxybenzyl group, a 2-formyloxybenzyl group, a 3-acetyloxybenzyl group, a 3-(2-acetyloxyphenyl)propyl group, a 4-(4-acetyloxyphenyl)butyl group, a 2-propionyloxybenzyl group, a 3-(3-butyryloxyphenyl)propyl group, a 4-(4-isobutyryloxyphenyl)butyl group, a 5-(2-tertbutylcarbonyloxyphenyl)pentyl group, a 6-(3-pentanoyloxyphenyl)hexyl group, a (2,4-diacetyloxy)benzyl group and the like.

The term "unsubstituted or lower alkyl-substituted amino group" as used herein refers to unsubstituted, mono- and dialkyl-substituted amino groups in which each alkyl moiety is a straight or branched chain alkyl group of 1 to 6 carbon atoms. As examples, there may be mentioned an amino group, a methylamino group, an ethylamino group, a propylamino group, an isopropylamino group, a n-butylamino group, a tert-butylamino group, a pentylamino group, a hexylamino group, a dimethylamino group, a diethylamino group, a dipropylamino group, a diisopropylamino group, a di-n- butylamino group, a dipentylamino group, a dihexylamino group, an N-methyl-N-ethylamino group, an N-methyl-N-propylamino group, an N-methyl-N-n-butylamino group, an N-ethyl-N-pentylamino group, an N-propyl-N-hexylamino group and the like.

The term "carboxy lower-alkoxy" as used herein refers to carboxyalkoxy groups whose alkoxy moiety is a straight or branched chain alkoxy group of 1 to 6 carbon atoms, such as a carboxymethoxy group, a 2-carboxyethoxy group, a 1-carboxyethoxy group, a 3-carboxypropoxy group, a 4-carboxybutoxy group, a 5-carboxypentyloxy group, a 6-carboxyhexyloxy group, a 1,1-dimethyl-2-carboxyethoxy group, a 2-methyl-3-carboxypropoxy group and the like.

The term "lower alkyl-substituted amino lower-alkyl group" as used herein refers to mono- and dialkyl-substituted aminoalkyl groups in which each alkyl moiety is a straight or branched chain alkyl group of 1 to 6 carbon atoms. As examples there may be mentioned a methylaminomethyl group, a 2-ethylaminoethyl group, a 1-propylaminoethyl group, a 3-isopropylaminopropyl group, a 4-n-butylaminobutyl group, a 5-tert-butylaminopentyl group, a 6-pentylaminohexyl group, a 1,1-dimethyl-2-hexylaminoethyl group, a dimethylaminomethyl group, a 2-methyl-3-diethylaminopropyl group, a dipropylaminomethyl group, a 2-diisopropylaminoethyl group, a 1-di-n-butylaminoethyl group, a 3-dipentylaminopropyl group, a 4-dihexylaminobutyl group, a 5-(N-methyl-N-ethylamino)pentyl group, a 6-(N-methyl-N-propylamino)hexyl group, a 1,1-dimethyl-2-(N-methyl-N-n-butylamino)ethyl group, a 2-methyl-3-(N-ethyl-N-pentylamino)propyl group, an (N-propyl-N-hexylamino)methyl group and the like.

The term "lower alkanoyloxy" as used herein refers to straight or branched chain alkanoyloxy groups of 1 to 6 carbon atoms, such as a formyloxy group, an acetyloxy group, a propionyloxy group, a butyryloxy group, a pentanoyloxy group, a hexanoyloxy group and the like.

The term "phenyl-lower alkoxy" as used herein refers to phenylalkoxy groups whose alkoxy moiety is a straight or branched chain alkoxy group of 1 to 6 carbon atoms, such as a benzyloxy group, a 2-phenylethoxy group, a 1-phenylethoxy group, a 3-phenylpropoxy group, a 4-phenylbutoxy group, a 5-phenylpentyloxy group, a 6-phenylhexyloxy group, a 1,1-dimethyl-2-phenylethoxy group, a 2-methyl-3-phenylpropoxy group and the like.

The term "phenyl-lower alkoxycarbonyl-lower alkoxy" as used herein refers to phenylalkoxycarbonylalkoxy groups whose two alkoxy moieties each is a straight or branched chain alkoxy group of 1 to 6 carbon atoms, such as a benzyloxycarbonylmethoxy group, a 2-(2-phenylethoxycarbonyl)ethoxy group, a 1-(1-phenylethoxycarbonyl)ethoxy group, a 3-(3-phenylpropoxycarbonyl)propoxy group, a 4-(4-phenylbutoxycarbonyl)butoxy group, a 1,1-dimethyl-2-(2-phenylethoxycarbonyl)ethoxy group, a 5-(5-phenylpentyloxycarbonyl)pentyloxy group, a 6-(6-phenylhexyloxycarbonyl)hexyloxy group, a 2-methyl-3-(3-phenylpropoxycarbonyl)propoxy group and the like.

The term "benzoyl group which may optionally be substituted, on the phenyl ring thereof, with at least one substituent selected from the group consisting of nitro, unsubstituted or lower alkyl-substituted amino, phenyl-lower alkoxy, hydroxy, carboxy, lower alkanoyloxy, carboxy-lower alkoxy, and lower alkyl-substituted amino-lower alkyl" as used herein refers to benzoyl groups which may be substituted with 1 to 3 substituents each selected from the group consisting of a nitro group, an amino group which may have one or two straight or branched chain alkyl groups of 1 to 6 carbon atoms, a phenylalkoxy group whose alkoxy moiety is a straight or branched chain alkoxy group of 1 to 6 carbon atoms, a hydroxy group, a carboxy group, a phenylalkoxycarbonylalkoxy group whose two alkoxy moieties each is a straight or branched chain alkoxy group of 1 to 6 carbon atoms, a straight or branched chain alkanoyloxy group of 1 to 6 carbon atoms, a carboxyalkoxy group whose alkoxy moiety is a straight or branched chain alkoxy group of 1 to 6 carbon atoms, or an aminoalkyl (a straight or branched chain alkyl group of 1 to 6 carbon atoms) which has one or two straight or branched chain alkyl groups of 1 to 6 carbon atoms. As examples of such benzoyl group there may be mentioned a benzoyl group, a 2-, 3- or 4-nitrobenzoyl group, a 2,4-dinitrobenzoyl group, a 2-, 3- or 4-aminobenzoyl group, a 2,4-diaminobenzoyl group, a 2-, 3- or 4-hydroxybenzoyl group, a 3,4-dihydroxybenzoyl group, a 2,3-dihydroxybenzoyl group, a 2,4-dihydroxybenzoyl group, a 2,6-dihydroxybenzoyl group, a 3,5-dihydroxybenzoyl group, a 2,5-dihydroxybenzoyl group, a 3,4,5-trihydroxybenzoyl group, a 2,4,6-trihydroxybenzoyl group, a 2-, 3- or 4-carboxybenzoyl group, a 2,4-dicarboxybenzoyl group, a 3,5-dicarboxybenzoyl group, a 2-, 3- or 4-benzyloxybenzoyl group, a 2-(2-phenylethoxy)benzoyl group, a 3-(1-phenylethoxy)benzoyl group, a 4-(3-phenylpropoxy)benzoyl group, a 3-(1,1-dimethyl-2-phenylethoxy)benzoyl group, a 4-(5-phenylpentyloxy)benzoyl group, a 3-(6-phenylhexyloxy)benzoyl group, a 3,4-dibenzyloxybenzoyl group, a 2,5-dibenzyloxybenzoyl group, a 3,4,5-tribenzyloxybenzoyl group, a 2-, 3- or 4-dimethylaminobenzoyl group, a 2-methylaminobenzoyl group, a 3-ethylaminobenzoyl group, a 4-propylaminobenzoyl group, a 2-isopropylaminobenzoyl group, a 3-n-butylaminobenzoyl group, a 4-tertbutylaminobenzoyl group, a 2-pentylaminobenzoyl group, a 3-hexylaminobenzoyl group, a 4-dipentylaminobenzoyl group, a 2-(N-methyl-N-n-butylamino)benzoyl group, a 3,5-di(dimethylamino)benzoyl group, a 2-, 3- or 4-acetyloxybenzoyl group, a 2- propionyloxybenzoyl group, a 3-butyryloxybenzoyl group, a 4-pentanoyloxybenzoyl group, a 2-hexanoyloxybenzoyl group, a 2,4-diacetyloxybenzoyl group, a 3,5-diacetyloxybenzoyl group, a 4-carboxymethoxybenzoyl group, a 2-(2-carboxyethoxy)benzoyl group, a 3-(1-carboxyethoxy)benzoyl group, a 2-(3-carboxypropoxy)benzoyl group, a 3-(4-carboxybutoxy)benzoyl group, a 4-(5-carboxypentyloxy)benzoyl group, a 2-(6-carboxyhexyloxy)benzoyl group, a 2,4-dicarboxymethoxybenzoyl group, a 2,6-dicarboxymethoxybenzoyl group, a 3,5-dicarboxymethoxybenzoyl group, a 2,5-dicarboxymethoxybenzoyl group, a 2,4,6-tricarboxymethoxybenzoyl group, a 4-hydroxy-3-dimethylaminomethylbenzoyl group, a 3-carboxymethoxy-5-hydroxybenzoyl group, a 3-hydroxy-5-dimethylaminomethylbenzoyl group, a 4-hydroxy-3-carboxymethoxybenzoyl group, a 4-carboxymethoxy-2-hydroxybenzoyl group, a 4-benzyloxycarbonylmethoxybenzoyl group, a 3-[2-(2-phenylethoxycarbonyl)ethoxy]benzoyl group, a 2-[1-(1-phenylethoxycarbonyl)ethoxy]benzoyl group, a 4-[3-(3-phenylpropoxycarbonyl)propoxy]benzoyl group, a 3-[4-(4-phenylbutoxycarbonyl)butoxy]benzoyl group, a 4-[5-(5-phenylpentyloxycarbonyl)pentyloxy]benzoyl group, a 2-[6-(6-phenylhexyloxycarbonyl)hexyloxy]benzoyl group, a 2,4-di(phenylmethoxycarbonylmethoxy)benzoyl group, a 3,5-di(phenylmethoxycarbonylmethoxy)benzoyl group, a 3,4-(diphenylmethoxycarbonylmethoxy)benzoyl group, a 2,4,6-tri(phenylmethoxycarbonylmethoxy)benzoyl group, a 4-methylaminomethylbenzoyl group, a 3-(2-ethylaminoethyl)benzoyl group, a 2-(1-propylaminoethyl)benzoyl group, a 3-(3-isopropylaminopropyl)benzoyl group, a 4-(4-n-butylaminobutyl)benzoyl group, a 2-(6-pentylaminohexyl)benzoyl group, a 2-(dimethylaminomethyl)benzoyl group, a 3-(3-diethylaminopropyl)benzoyl group, a 4-[5-(N-methyl-N-ethylamino)pentyl]benzoyl group, a 2-[6-(N-methyl-N-propylamino)hexyl]benzoyl group, and the like.

The term "naphthoyl group" as used herein refers to a 1-naphthoyl group, a 2-naphthoyl group and the like.

The term "lower alkoxy" as used herein refers to straight or branched chain alkoxy groups of 1 to 6 carbon atoms such as a methoxy group, an ethoxy group, a propoxy group, an isopropoxy group, a n-butoxy group, a tert-butoxy group, a pentyloxy group, a hexyloxy group and the like.

The term "benzoyl group which may optionally have, on the phenyl ring thereof, at least one alkoxy group" as used herein refers to benzoyl groups which may have one or two straight or branched chain alkoxy groups of 1 to 6 carbon atoms. As examples there may be mentioned a benzoyl group, a 2-, 3- or 4-methoxybenzoyl group, a 2-, 3- or 4-ethoxybenzoyl group, a 4-isopropoxybenzoyl group, a 4-pentyloxybenzoyl group, a 4-hexyloxybenzoyl group, a 3,4-dimethoxybenzoyl group, a 3,4-diethoxybenzoyl group, a 2,5-dimethoxybenzoyl group, a 2,6-dimethoxybenzoyl group and the like.

The compounds of this invention can be prepared by various alternative processes, among which are the processes described below by reference to reaction schemes.

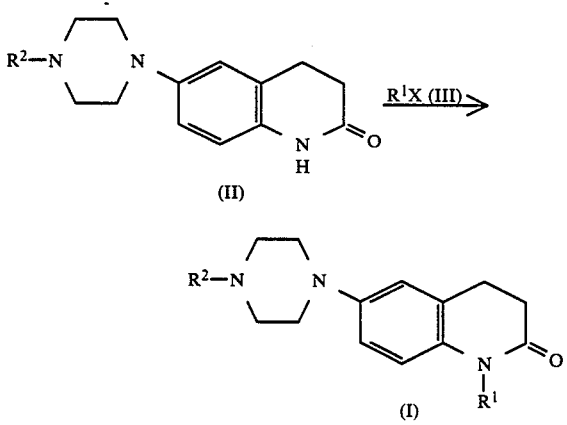

In the above formulas, R¹ and R² are each as defined above and X is a halogen atom.

The reaction between the compound of the formula (II) and the compound of the formula (III) is conducted in the presence of a basic compound in a suitable solvent. Examples of the basic compound include alkali metal compounds such as sodium hydride, metallic potassium, metallic sodium, sodium amide, potassium amide, etc., lithium compounds such as metallic lithium, n-butyllithium, etc. and the like. Examples of the solvent include ethers such as dioxane, diethylene glycol dimethyl ether, diethyl ether, tetrahydrofuran, etc., aromatic hydrocarbons such as benzene, toluene, xylene, etc., polar solvents such as dimethylformamide, dimethyl sulfoxide, hexamethylphosphoric triamide, etc. and the like. The compound of the formula (III) is used generally in an amount of at least 1 mole, preferably about 1 to 2 moles, per mole of the compound of the formula (II). Generally, the reaction proceeds within the temperature range of −20° to 70° C., preferably −20° C. to about room temperature, and comes to an end in a few minutes to about 12 hours.

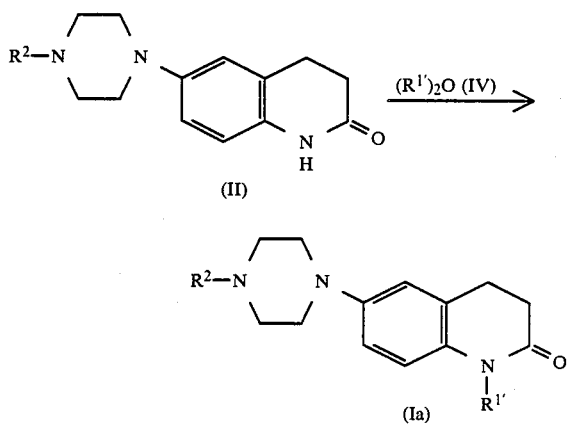

In the above formulas, R² is as defined above, and R¹' is a lower alkanoyl group, a lower alkoxycarbonyl group, or a benzoyl group which may optionally be substituted, on the phenyl ring thereof, with at least one substituent selected from the group consisting of nitro, unsubstituted or lower alkyl-substituted amino, phenyl-lower alkoxy, hydroxy, carboxy, phenyl-lower alkoxycarbonyl-lower alkoxy, lower alkanoyloxy, carboxy-lower alkoxy, and lower alkyl-substituted amino-lower alkyl.

The reaction between the compound of the formula (II) and the compound of the formula (IV) can be conducted under the same conditions as in the reaction between the compound of the formula (II) and the compound of the formula (III).

In the case where R¹ is a phenyl-lower alkyl group which has, as a substituent on the phenyl ring thereof, at least one lower alkanoyloxy group or a benzoyl group which has, on the phenyl ring thereof, at least one phenyl-lower alkoxy group, the compound of the formula (I), upon hydrolysis or catalytic reduction, gives a compound of the formula (I) wherein R¹ is a phenyl-lower alkyl or benzoyl group which has, as a substituent on the phenyl ring thereof, at least one hydroxy group.

The above hydrolysis reaction (de-lower alkanoylation reaction) is conducted in a suitable solvent in the presence of an acid or a basic compound. Examples of the solvent include water, alcohols such as methanol, ethanol, isopropanol, etc., ethers such as dioxane, tetrahydrofuran, etc., and mixtures thereof, and the like. The acid includes mineral acids such as hydrochloric acid, sulfuric acid, hydrobromic acid, etc., and the basic compound includes metal hydroxides such as sodium hydroxide, potassium hydroxide, calcium hydroxide, etc., metal carbonates or hydrogen carbonates such as potassium carbonate, sodium carbonate, sodium hydrogen carbonate, etc. Generally, the reaction proceeds within the temperature range of 0°–150° C., preferably around room temperature to 100° C., and comes to an end in about 10 minutes to 15 hours.

For the above catalytic reduction (dephenyl-lower alkylation reaction), a wide variety of usual dephenyl-lower alkylation reaction conditions can be employed. For example, the reduction is conducted in a suitable solvent in the presence of a catalyst such as palladium on carbon, palladium black, platinum black and the like within the temperature range of 0° C. to 100° C. for about 0.5 to 5 hours. As examples of the solvent, there may be mentioned water, lower alcohols such as methanol, ethanol, isopropanol, etc., ethers such as dioxane, tetrahydrofuran, etc., polar solvents such as acetic acid, dimethylformamide, etc., and mixtures thereof, and the like. The catalyst is used generally in an amount of 10 to 50 weight % based on the starting compound. The reaction can be accelerated by addition, to the reaction system, of an acid such as concentrated hydrochloric acid, etc.

The compound of the formula (I) wherein $R^1$ is a benzoyl group which has, as a substituent on the phenyl ring thereof, at least one amino group can be prepared also by reducing the corresponding compound wherein $R^1$ is a benzoyl group which has, as a substituent on the phenyl ring thereof, at least one nitro group.

For the above reduction, a wide variety of usual conditions for reducing an aromatic nitro group to an aromatic amino group can be employed. The reaction is conducted in the manner of, for example, (1) reduction in a suitable solvent using a catalyst or (2) reduction in an inert solvent using, as the reducing agent, a mixture of a metal or metal salt and an acid or of a metal or metal salt and an alkali metal hydroxide, a sulfide, an ammonium salt or the like.

Examples of the solvent for use in the catalytic reduction (1) include water, acetic acid, alcohols such as methanol, ethanol, isopropanol, etc., hydrocarbons such as hexane, cyclohexane, etc., ethers such as diethylene glycol dimethyl ether, dioxane, tetrahydrofuran, diethyl ether, etc., esters such as ethyl acetate, methyl acetate, etc., aprotic polar solvents such as dimethylformamide, etc., mixtures thereof, and the like. Examples of the catalyst include palladium black, palladium on carbon, platinum, platinum oxide, copper chromite, Raney nickel and the like. The catalyst is used preferably in an amount of 0.02 to 1.00 part by weight per part by weight of the starting compound. Generally, the reaction proceeds within the temperature range of −20° to 100° C., preferably 0 to 70° C., at a hydrogen pressure of 1 to 10 atmospheres and comes to an end in about 0.5 to 10 hours.

In carrying out the reduction (2), there is used, as the reducing agent, a mixture of iron, zinc, tin or stannous chloride and a mineral acid such as hydrochloric acid, sulfuric acid, etc., or a mixture of iron, ferrous sulfate, zinc or tin and an alkali metal hydroxide such as sodium hydroxide, etc., a sulfide such as ammonium sulfide, etc., aqueous ammonia or an ammonium salt such as ammonium chloride, etc., for instance. Examples of the inert solvent include water, acetic acid, methanol, ethanol, dioxane and the like. The reduction conditions may be selected according to the kind of the reducing agent to be used. Generally, the reaction proceeds within the temperature range of −50° to 100° C. and comes to an end in about 0.5 to 10 hours. When a mixture of stannous chloride and hydrochloric acid, for instance, is used as the reducing agent, the reaction is conducted advantageously within the temperature range of about −20° to 70° C. The reducing agent is used in an amount of at least 1 mole, generally 1 to 3 moles, per mole of the starting compound.

The compound of the formula (I) wherein $R^1$ is a benzoyl group which has, on the phenyl ring thereof, at least one carboxy-lower alkoxy group or phenyl-lower alkoxycarbonyl-lower alkoxy group is obtained by reacting a compound of the formula (I) wherein $R^1$ is a benzoyl group which has, on the phenyl ring thereof, at least one hydroxy group with a monohalo-lower alkanoic acid (e.g. chloroacetic acid, bromoacetic acid, chloropropionic acid, etc.) or a monohalo-lower alkanoic acid phenyl-lower alkyl ester (e.g. benzyl chloroacetate, benzyl bromoacetate, benzyl bromopropionate, etc.).

When a monohalo-lower alkanoic acid phenyllower alkyl ester is used and the product is further subjected to hydrolysis or catalytic reduction, the group $R^1$ can be converted to a benzoyl group having a carboxy-lower alkoxy group.

The reaction can be carried out in a solvent in the presence of a basic compound. As the solvent, any solvent that will not adversely affect the reaction can be used. Examples of such solvent include aromatic hydrocarbons such as benzene, toluene, xylene, etc., ethers such as dioxane, diethylene glycol dimethyl ether, diethyl ether, tetrahydrofuran, etc., halogenated hydrocarbons such as chloroform, dichloromethane, carbon tetrachloride, etc., aprotic polar solvents such as dimethylformamide, dimethyl sulfoxide, hexamethylphosphoric triamide, etc. and the like. As examples of the basic compound, there may be mentioned organic bases such as triethylamine, pyridine, N,N-dimethylaniline, 1,5-diazobicyclo[4.3.0]nonene-5 (DBN), 1,8-diazabicyclo[5.4.0]undecene-7 (DBU), 1,4-diazabicyclo[2.2.2]octane (DANCO), etc. and inorganic bases such as sodium hydrogen carbonate, potassium hydrogen carbonate, sodium carbonate, potassium carbonate, sodium hydroxide, potassium hydroxide, etc.

Generally, the reaction proceeds in the temeperature range of 0°–150° C., preferably about room temperature to 100° C., and comes to an end in about 1 to 20 hours.

The monohaloalkanoic acid or monohaloalkanoic acid phenyl-lower alkyl ester is used in an amount of at least 1 mole, preferably 1 to 5 moles, per mole of the starting material.

The hydrolysis or catalytic reduction of the monohalo-lower alkanoic acid phenyl-lower alkyl ester-derived moiety, if such is desired subsequently, can be conducted under the same conditions as in the hydrolysis or catalytic reduction of the compound of the formula (I) wherein $R^2$ is a phenyl-lower alkyl group which has, as a substituent on the phenyl ring thereof, at least one lower alkanoloxy group or a benzoyl group which has, on the phenyl ring thereof, at least one phenyl-lower alkoxy group.

The compound of the formula (I) wherein $R^1$ is a benzoyl group which has, as a substituent on the phenyl ring thereof, at least one lower alkyl-substituted amino-lower alkyl group can be obtained by reacting a compound of the formula (I) wherein $R^1$ is a benzoyl group which has, as a substituent on the phenyl ring thereof, at least one substituent selected from among hydroxy and unsubstituted or lower alkyl-substituted amino groups, with (1) a compound of the formula

and formaldehyde or (2) a compound of the formula

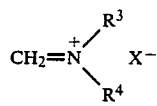

wherein $R^3$ is a hydrogen atom or a lower alkyl group, $R^4$ is a lower alkyl group and X is as defined above.

The above reaction (1) is generally called as Mannich reaction and can be conducted in the presence of an acid and in a suitable solvent.

As the solvent, any solvent that is usually used in the Mannich reaction can be used. As examples of such solvent there may be mentioned water, alcohols such as methanol, ethanol, isopropanol, etc., alkanoic acids such as acetic acid, propionic acid, etc., acid anhydrides such as acetic anhydride, etc., polar solvents such as acetone, dimethylformamide, etc., mixtures thereof, and the like. Examples of the acid include mineral acids such as hydrochloric acid, hydrobromic acid, etc. and organic acids such as acetic acid, etc. As the formaldehyde, an aqueous 20–40 weight % formaldehyde-containing solution, trioxane, a polymeric form of formaldehyde (paraformaldehyde) or the like is usually used.

The compound of the formula

is used in an amount of at least 1 mole, preferably 1 to 2 moles, per mole of the starting material. The formaldehyde is used in an at least equimolar amount, preferably in a large excess, based on the starting compound. Generally, the reaction proceeds within the temperature range of 0°–200° C., preferably about room temperature to 150° C., and comes to an end in about 0.5 to 10 hours.

The above reaction (2) can be conducted in a suitable solvent in the presence or absence of a basic compound. As the solvent or basic compound, there can be used the same solvent or basic compound as mentioned in relation to the production of the compound of the formula (I) wherein $R^1$ is a benzoyl group which has at least one carboxy-lower alkoxy group.

Generally, the reaction proceeds within the temperature range of 0–150° C., preferably about room temperature to 100° C., and comes to an end in about 1 to 20 hours. The compound of the formula

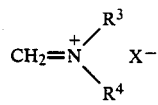

is used in an amount of at least 1 mole, preferably 1 to 3 moles, per mole of the starting material.

The compound of the formula (I) wherein $R^1$ is a phenyl-lower alkyl group which has, on the phenyl ring thereof, at least one lower alkanoyloxy group or a benzoyl group which has, on the phenyl ring thereof, at least one lower alkanoyloxy group can also be obtained by subjecting a compound of the formula (I) wherein $R^1$ is a phenyl-lower alkyl group which has, on the phenyl ring thereof, at least one hydroxy group or a benzoyl group which has, on the phenyl ring thereof, at least one hydroxy group to acylation reaction.

The acylation reaction is conducted in the conventional manner using, as the acylating agent, an alkanoic acid halide of 1 to 6 carbon atoms or an acid anhydride such as alkanoic acid anhydride of 1 to 6 carbon atoms and the like.

The reaction using an acid halide is conducted in an inert solvent using, if necessary, a dehydrohalogenating agent, e.g. an amine such as triethylamine, diisopropylethylamine, pyridine, N,N-diethylaniline, and the like, within the temperature range of −50° to 150° C. for 1 to 24 hours.

The reaction using an acid anhydride is conducted in an inert solvent using, if necessary, a dehydrohalogenating agent such as mentioned above, within the temperature range of room temperature to 200° C. for about 1 to 10 hours. As the inert solvent for the above reactions, such solvents as aromatic hydrocarbons (e.g. nitrobenzene, chlorobenzene, etc.), amines (e.g. pyridine, N,N-dimethylaniline, etc.), ethers (e.g. ethyl ether, etc.), halogenated hydrocarbons (e.g. dichloromethane, dichloroethane, chloroform, etc.) and the like can be used. The acylating agent is used generally in an amount of at least 1 mole, preferably 1 to large excess moles, per 1 mole of the above starting material.

Those carbostyril derivatives of this invention of the formula (I) which are basic each can easily be converted to an acid addition salt by reaction with a usual pharmaceutically acceptable acid. As examples of the acid, there may be mentioned inorganic acids such as hydrochloric acid, sulfuric acid, phosphoric acid, hydrobromic acid, and the like and organic acids such as oxalic acid, maleic acid, fumaric acid, malic acid, tartaric acid, citric acid, benzoic acid and the like.

Those carbostyril derivatives of this invention of the formula (I) which are acid each can easily form a salt with a pharmaceutically acceptable base. Examples of the base include metal hydroxides such as sodium hydroxide, potassium hydroxide, calcium hydroxide and the like, alkali metal carbonates or hydrogen carbonates such as sodium carbonate, sodium hydrogen carbonate and the like, and alkali metal alcoholates such as sodium methylate, potassium ethylate and the like.

The compounds of this invention which are in the salt form or have a hydrophilic residue in the position 1 show very good water solubility, retain their potent myocardial contractility-increasing activity in vivo, scarcely produce adverse effects, and can be used in the form of injections very favorably.

The desired compounds obtained in the above processes can be easily isolated and purified by some or other conventional separation technique. Examples of the separation technique include solvent extraction, dilution, recrystallization, column chromatography, preparative thin-layer chromatography and the like.

It is to be noted that, as a matter of course, all possible optical isomers also fall within the scope of this invention.

In using the compounds of this invention of the formula (I) and the salts therof as therapeutic agents, these compounds can be formulated into pharmaceutical compositions together with ordinary pharmaceutically acceptable carriers. Suitable carriers which can be used are, for example, solvents, wetting agents, disintegrants, surface active agents and lubricants which are usually employed to prepare such drugs depending on the type of dosage form.

Various dosage forms of the therapeutic agents as a cardiotonic agent can be selected according to the purpose of the therapy. Typical dosage forms which can be used are tablets, pills, powders, liquid preparations, suspensions, emulsions, granules, capsules, suppositories, and injectable preparations (solutions, suspensions, etc.).

In molding a pharmaceutical composition containing the compounds of the formula (I) or the pharmaceutically acceptable salt thereof as an active ingredient into a tablet form, a wide range of carriers known in the art can be used. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dired starch, sodium alginate, agar powder, laminaria powder, sodium hydrogencarbonate, calcium carbonate, Tween, sodium laurylsulfate, stearic acid monoglyceride, starch, and lactose, disintegration inhibitors such as white sugar, stearic acid glyceryl ester, cacao butter and hydrogenated oils, absorption promotors such as quaternary ammonium bases and sodium laurylsulfate, humectants such as glycerol and starch, adsorbents such as starch, lactose, kaolin, bentonite and colloidal silicic acid, and lubricants such as purified talc, stearic acid salts, boric acid powder, Macrogol (trade name for a polyethylene glycol produced by Shinetsu Chemical Industry Co., Ltd.) and solid polyethylene glycol.

The tablets, if desired, can be coated, and made into sugar-coated tablets, gelatin-coated tablets, enteric-coated tablets, film-coated tablets, or tablets comprising two or more layers.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, esters of higher alcohols, gelatin, and semisynthetic glycerides.

When the pharmaceutical composition is formulated into an injectable preparation, the resulting solution and suspension are preferably sterilized, and are isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a cardiotonic agent, in an amount sufficient to prepare isotonic solutions. The cardiotonic agent may further contain ordinary dissolving aids, buffers, painalleviating agents, and preservatives, and optionally coloring agents, perfumes, flavors, sweeteners, and other drugs.

The amount of the compound of the formula (I) and the pharmaceutically acceptable salts thereof of this invention as an active ingredient to be incorporated into a pharmaceutical composition useful as a cardiotonic agent is not particularly limited, and can vary over a wide range. A suitable therapeutically effective amount of the compound of the general formula (I) and the pharmaceutically acceptable salts thereof of this invention is usually about 1 to about 70% by weight, preferably 1 to 30% by weight, based on the entire composition.

The administration method of the cardiotonic agent according to the invention is not particularly limited and can be adequately selected according to the form of the preparation, age and sex of the patient, and symptom of disease. For example, the tablets, pills, liquid preparations, suspensions, emulsions, granules, and capsules are orally administered. The injectable preparations are intravenously adminstered either alone or together with ordinary auxiliary agents such as glucose and amino acids. Furthermore, as required, the cardiotonic agent can be singly adminstered intramuscularly, intracutaneously, subcutaneously, or intraperitoneally. The suppository is administered intrarectally.

The dosage of the cardiotonic agent is suitably selected according to the purpose of use, age and sex of the patient, and the symptoms of disease, etc. Usually, a preferred dosage of the compound of this invention is about 0.1 to 10 mg/kg weight per day. It is advantageous that the active ingredient is contained in a single unit dose form in an amount of 2 to 200 mg.

Hereinafter, this invention will be described in greater detail with reference to Examples and Preparation Examples.

EXAMPLES

Example 1

Sodium hydride (60% in oil, 263 mg) was suspended in dimethylformamide (DMF) (30 ml). To the suspension was added 6-[4-(3,4-dimethoxybenzoyl)-1-piperazinyl]-3,4-dihydrocarbostyril (2 g) and the mixture was stirred at 70° to 80° C. for 30 minutes. After cooling, to the mixture was added slowly acetyl chloride (0.43 m/g) with stirring and under ice-cooling, and the mixture was stirred at the same temperature for 5 minutes. After completion of reaction, the reaction mixture was poured into ice-water and extracted with chloroform. The chloroform layer was washed successively with water and saturated saline solution and dried over magnesium sulfate. The chloroform extract was evaporated under reduced pressure. The resultant residue was purified by silica-gel column chromatography (eluent:dichloromethane:methanol=100:1) and recrystallized from a mixture of dichloromethane and diethyl ether to give 1-acetyl-6-[4-(3,4-dimethoxybenzoyl)-1-piperazinyl]-3,4-dihydrocarbostyril (700 mg).

m.p. 192° to 194° C. (decomposed)

colorless prisms

Examples 2 to 25

In an analogous manner as Example 1, the compounds shown in Table 1 were prepared using appropriate starting materials.

TABLE 1

[Structure: piperazine-N-R² substituted 3,4-dihydroquinolin-2(1H)-one with N-R¹]

| Example No. | R¹ | R² | m.p. (°C.) (Recrystallization solvent) | Crystal form |
|---|---|---|---|---|
| 2 | $-CO_2C_2H_5$ | $-CO$-(2,5-dimethoxyphenyl) with $OCH_3$, $OCH_3$ | 120–121 (dichloromethane-diethyl ether) | colorless prisms |
| 3 | $-CH_2CO_2C_2H_5$ | $-CO$-(2,5-dimethoxyphenyl) | 158–160 (ethanol) | colorless prisms |
| 4 | $-CH_2$-C$_6$H$_4$-$OCCH_3$ (para, $\|$ O) | $-CO$-(2,5-dimethoxyphenyl) | 123–126 (ethanol) | colorless prisms |
| 5 | $-CH_2$-C$_6$H$_4$-OH | $-CO$-(2,5-dimethoxyphenyl) | 203–204 (ethanol) | colorless prisms |
| 6 | $-CO$-C$_6$H$_4$-$NO_2$ | $-CO$-(2,5-dimethoxyphenyl) | NMR[1] | |
| 7 | $-CO$-C$_6$H$_4$-$NH_2$ | $-CO$-(2,5-dimethoxyphenyl) | 197–198 (ethanol) | colorless prisms |
| 8 | $-CO$-C$_6$H$_4$-$OCH_2Ph$ | $-CO$-(2,5-dimethoxyphenyl) | NMR[2] | |
| 9 | $-CO$-C$_6$H$_4$-OH | $-CO$-(2,5-dimethoxyphenyl) | 114–134[3] (decomposed) | yellow powder |
| 10 | $-CO$-C$_6$H$_4$-OH | $-CO$-(2,5-dimethoxyphenyl) | 122–145[4] (decomposed) | yellow powder |

TABLE 1-continued
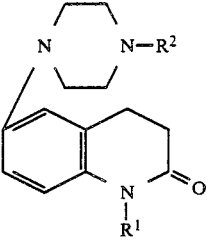
| Example No. | R¹ | R² | m.p. (°C.) (Recrystallization solvent) | Crystal form |
|---|---|---|---|---|
| 11 | 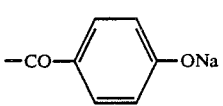 | 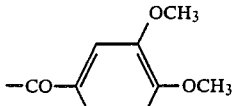 | 97–115[5] (decomposed) | yellow powder |
| 12 | 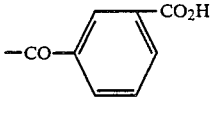 | 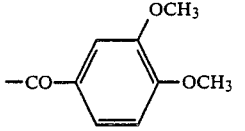 | 120–141[6] (decomposed) | yellow powder |
| 13 | 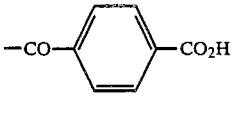 | 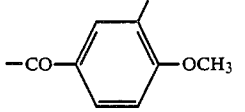 | 123–150[7] (decomposed) | yellow powder |
| 14 | 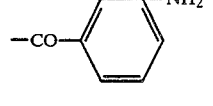 | 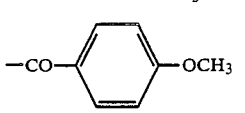 | 118–126[8] (ethanol, decomposed) | colorless powder ½ hydrate |
| 15 | 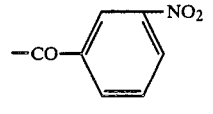 | 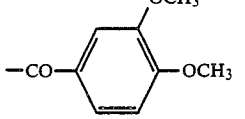 | 98–104[9] (ethanol, decomposed) | yellow powder |
| 16 | 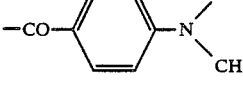 | 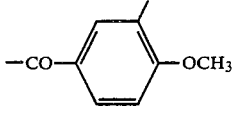 | NMR[10] | yellow crystal |
| 17 | 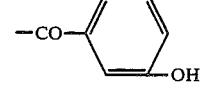 | 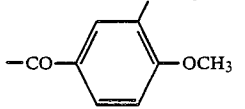 | NMR[11] | yellow crystal |
| 18 | 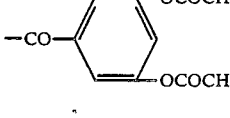 | 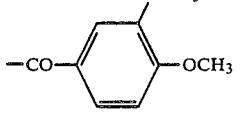 | NMR[12] | yellow crystal |
| 19 | 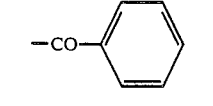 | 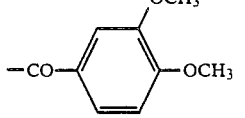 | NMR[13] | yellow crystal |

TABLE 1-continued

[Core structure: 3,4-dihydroquinolin-2(1H)-one with piperazinyl substituent at position 6 (N-R² on distal piperazine N), and R¹ on the lactam nitrogen]

| Example No. | R¹ | R² | m.p. (°C.) (Recrystallization solvent) | Crystal form |
|---|---|---|---|---|
| 20 | −CO−C₆H₄−OCH₂CO(OCH₂Ph) (para) | −CO−C₆H₃(OCH₃)₂ (2,5-dimethoxybenzoyl) | NMR¹⁴ | yellow crystal |
| 21 | −CO−C₆H₄−OCH₂CO₂H (para) | −CO−C₆H₃(OCH₃)₂ (2,5-dimethoxybenzoyl) | NMR¹⁵ | yellow crystal |
| 22 | −CO−C₆H₃(OH)₂ (2,5-dihydroxybenzoyl) | −CO−C₆H₃(OCH₃)₂ (2,5-dimethoxybenzoyl) | NMR¹⁶ | yellow crystal |
| 23 | −CO−C₆H₃(CH₂N(CH₃)₂)(OH) (3-dimethylaminomethyl-4-hydroxybenzoyl) | −CO−C₆H₃(OCH₃)₂ (2,5-dimethoxybenzoyl) | NMR¹⁷ | yellow crystal |
| 24 | −CO−(1-naphthyl) | −CO−C₆H₃(OCH₃)₂ (2,5-dimethoxybenzoyl) | NMR¹⁸ | yellow crystal |
| 25 | −CO−C₆H₃(OH)(OCH₂CO₂H) | −CO−C₆H₃(OCH₃)₂ (2,5-dimethoxybenzoyl) | NMR¹⁹ | yellow crystal |

(1) NMR (CDCl₃) δ: 2.60–2.90 (m, 2H), 2.90–3.20 (m, 2H), 3.0–3.31 (m, 4H), 3.60–3.98 (m, 4H), 3.90 (s, 6H), 6.60–7.14 (m, 4H), 7.86 (d, 2H, J=9Hz), 8.28 (d, 2H, J=9Hz)

(2) NMR (CDCl₃) δ: 2.52–3.30 (m, 8H), 3.65–3.92 (m, 4H), 3.90 (s, 6H), 5.10 (s, 2H), 6.65–7.60 (m, 15H)

(3) NMR (CDCl₃) δ: 2.52–2.85 (m, 2H), 2.85–3.15 (m, 2H), 2.90–3.30 (m, 4H), 3.60–4.10 (m, 4H), 3.82 (s, 3H), 3.88 (s, 3H), 6.65–7.40 (m, 10H).
IR $\nu_{max}^{KBr}$: 3430, 1725, 1630, 1610, 1585, 1505, 1435, 1290, 1270, 1230, 1020 cm⁻¹

(4) NMR (DMSO-d₆) δ: 2.60–2.75 (m, 2H), 2.90–3.20 (m, 6H), 3.50–3.75 (m, 4H), 3.79 (s, 3H), 3.81 (s, 3H), 6.48 (d, 1H, J=9.0Hz), 6.75 (d-d, 1H, J=9.0Hz, J=2.5Hz), 6.88 (d, 2H, J=8.5Hz), 6.99 (d, 1H, J=2.5Hz), 7.01 (s, 3H), 7.77 (d, 2H, J=8.5Hz)
IR $\nu_{max}^{KBr}$: 1725, 1630, 1610, 1585, 1505, 1435, 1290, 1270, 1230, 1020 cm⁻¹

(5) NMR (DMSO-d₆) δ: 2.50–2.70 (m, 2H), 2.90–3.05 (m, 2H), 3.05–3.25 (m, 4H), 3.5–3.75 (m, 4H), 3.82 (s, 3H), 3.84 (s, 3H), 6.05 (d, 2H, J=9.0Hz), 6.55 (d-d, 1H, J=9.0Hz, J=2.5Hz), 6.95 (d, 1H, J=2.5Hz), 7.04 (s, 3H), 7.36 (d, 2H, J=9.0Hz)
IR $\nu_{max}^{KBr}$: 3450, 1580, 1505, 1440, 1340, 1285, 1235, 1160, 1020, 875 cm⁻¹

(6) NMR (DMSO-d₆) δ: 2.7–2.85 (m, 2H), 2.95–3.3 (m, 6H), 3.7–3.9 (m, 4H), 3.90 (s, 3H), 3.91 (s, 3H), 6.6–7.1 (m, 6H), 7.57 (t, 1H, J=8.0Hz), 8.06 (d-m, 1H, J=8Hz), 8.27 (d-m, 1H, J=8Hz), 8.48 (m, 1H)

IR $\nu_{max}^{KBr}$: 3450, 2940, 2840, 1720, 1605, 1580, 1505, 1470, 1435, 1270, 1235, 1020 cm$^{-1}$ (7) NMR (CDCl$_3$) δ: 2.52-2.90 (m, 2H), 2.90-3.40 (m, 6H), 3.60-4.0 (m, 4H), 3.90 (s, 6H), 6.60-7.20 (m, 6H), 7.86 (d, 2H, J=8Hz), 8.15 (d, 2H, J=8Hz)

IR $\nu_{max}^{KBr}$: 3450, 2940, 2840, 1720, 1605, 1580, 1505, 1470, 1435, 1270, 1235, 1020 cm$^{-1}$ (8) NMR (CDCl$_3$) δ: 2.65-2.85 (m, 2H), 2.85-3.30 (m, 6H), 3.66-4.00 (m, 6H), 3.90 (s, 6H), 6.60-7.30 (m, 10H)

IR $\nu_{max}^{KBr}$: 3450, 3375, 1720, 1670, 1630, 1610, 1515, 1435, 1270, 1235, 1140, 1025 cm$^{-1}$ (9) NMR (CDCl$_3$) δ: 2.65-2.90 (m, 2H), 2.90-3.33 (m 6H), 3.60-4.00 (m, 4H), 3.90 (s, 6H), 6.60-7.10 (m, 6H), 7.65 (m, 1H), 8.10 (m, 1H), 8.45 (m, 1H), 8.57 (m, 1H)

IR $\nu_{max}^{KBr}$: 1680, 1635, 1535, 1435, 1355, 1270, 1240, 1230, 1025, 660 cm$^{-1}$

(10) NMR (CDCl$_3$) δ: 2.72-2.79 (m, 2H), 3.06 (s, 6H), 2.88-3.19 (m, 6H), 3.70-3.92 (m, 4H), 3.90 (s, 3H), 3.97 (s, 3H), 6.59-7.02 (m, 8H), 7.79 (d, 2H, J=8Hz)

(11) NMR (DMSO-d$_6$) δ: 2.32-2.92 (m, 4H), 2.90-3.40 (m, 4H), 3.40-3.80 (m, 4H), 3.82 (s, 6H), 6.32-7.20 (m, 9H)

(12) NMR (CDCl$_3$) δ: 2.28 (s, 6H), 2.50-2.90 (m, 2H), 2.82-3.30 (m, 6H), 3.60-4.00 (m, 4H), 3.90 (s, 6H), 6.65-7.50 (m, 9H)

(13) NMR (CDCl$_3$) δ: 2.62-2.93 (m, 2H), 2.93-3.50 (m, 6H), 3.70-4.00 (m, 4H), 3.90 (s, 6H), 6.70-7.90 (m, 11H)

(14) NMR (CDCl$_3$) δ: 2.60-2.90 (m, 2H), 2.90-3.30 (m, 6H), 3.60-4.00 (m, 4H), 3.90 (s, 6H), 4.70 (s, 2H), 5.21 (s, 2H), 6.70-7.10 (m, 8H), 7.34 (s, 5H), 7.82 (d, 2H, J=9Hz)

(15) NMR (CDCl$_3$) δ: 2.68-2.81 (m, 2H), 2.90-3.30 (m, 6H), 3.60-3.90 (m, 4H), 3.88 (s, 3H), 3.91 (s, 3H), 4.63 (brs, 2H), 6.60-7.05 (m, 8H), 7.82 (d, 2H, J=9Hz)

(16) NMR (CDCl$_3$) δ: 2.76-2.83 (m, 2H), 3.03-3.15 (m, 6H), 3.69-3.91 (brs, 4H), 3.89 (s, 3H), 3.91 (s, 3H), 6.24 (s, 1H), 6.26 (d-d, 1H, J=2.4Hz, 10Hz), 6.66-7.03 (m, 6H), 7.23 (d, 1H, J=10Hz), 8.41 (brs, 1H), 11.15 (s, 1H)

(17) NMR (CDCl$_3$) δ: 2.34 (s, 6H), 2.60-2.90 (m, 2H), 2.90-3.30 (m, 6H), 3.70 (s, 2H), 3.65-3.90 (m, 4H), 3.90 (s, 6H), 6.65-7.11 (m, 7H), 7.65 (d-d, 1H, J=2Hz, 8Hz), 7.78 (s, 1H)

(18) NMR (CDCl$_3$) δ: 2.52-2.82 (m, 2H), 2.82-3.30 (m, 6H), 3.60-4.10 (m, 4H), 3.88 (s, 6H), 6.65 (m, 12H), 8.50-8.70 (m, 1H)

(19) NMR (DMSO-d$_6$) δ: 2.50-3.00 (m, 2H), 2.70-3.30 (m, 6H), 3.80 (s, 6H), 4.68 (s, 2H), 6.50-7.10 (m, 9H)

Example 26

To a suspension of 6-[4-(3,4-dimethoxybenzoyl)-1-piperazinyl]-3,4-dihydrocarbostyril (10 g) in anhydrous tetrahydrofuran (250 ml) was added slowly n-butyllithium (20 ml, 1.5N hexane solution) with stirring and under ice-cooling. After completion of addition, the mixture was stirred at room temperature for 2 hours. Then, to the mixture was added slowly a solution of p-nitrobenzoyl chloride (6.1 g) in anhydrous tetrahydrofuran (25 ml) with stirring and under ice-cooling. After completion of addition, the mixture was stirred at the same temperature for 30 minutes. After completion of reaction, the reaction mixture was poured into water and extracted with chloroform. The chloroform layer was washed successively with water and saturated saline solution and dried over magnesium sulfate. The choloroform extract was evaporated under reduced pressure and the resultant residue was purified by silica-gel column chromatography (eluent:dichloromethane:methanol=100:1) to give 1-(4-nitrobenzoyl)-6-[4-(3,4-dimethoxybenzoyl)-1-piperazinyl]3,4-dihydrocarbostyril (2.6 g).

NMR (CDCl$_3$) δ: 2.60-2.90 (m, 2H), 2.90-3.20 (m, 2H), 3.0-3.31 (m, 4H), 3.60-3.98 (m, 4H), 3.90 (s, 6H), 6.60-7.14 (m, 4H), 7.86 (d, 2H, J=9Hz), 8.28 (d, 2H, J=9Hz)

Example 27

1-(4-Acetoxybenzyl)-6-[4-(3,4-dimethoxybenzoyl)-1-piperazinyl]-3,4-dihydrocarbostyril (2 g) was dissolved in methanol (20 ml). To the solution was added a solution of potassium carbonate (1.53 g) in water (20 ml) and the mixture was stirred at room temperature for 30 minutes. After completion of reaction, the reaction mixture was poured into water and extracted with chloroform. The extract was washed with saturated saline solution, dried over magnesium sulfate and evaporated under reduced pressure. The residue was recrystallized from ethanol to give 1-(4-hydroxybenzyl)-6-[4-(3,4-dimethoxybenzoyl)-1-piperazinyl]-3,4-dihydrocarbostyril (950 mg).

m.p. 203° to 204° C.

colorless prisms

Example 28

To a mixture of 1-(4-nitrobenzoyl)-6-[4-(3,4-dimethoxybenzoyl)-1-piperazinyl]-3,4-dihydrocarbostyril (1.5 g) and ethanol (30 ml) were added DMF (5 ml) and 10% palladium on carbon (300 mg). The mixture was hydrogenated at 50° to 60° C. After competion of reaction, the catalyst was filtered off and the filtrate was evaporated under reduced pressure. The resultant residue was purified by silica-gel column chromatography (eluent:dichloromethane:methanol= 100:2) and recrystallized from ethanol to give 1-(4-aminobenzoyl)-6-[4-(3,4-dimethoxybenzoyl)-1-piperazinyl]-3,4-dihydrocarbostyril (0.45 g).

m.p. 197° to 198° C.

colorless prisms

In an analogous manner as Example 28, the same compound as that obtained in Example 14 mentioned before was prepared using appropriate starting materials.

Example 29

1-(3-Benzyloxybenzoyl)-6-[4-(3,4-dimethoxybenzoyl)-1-piperazinyl]-3,4-dihydrocarbostyril (6 g) was dissolved in a mixture of ethanol (100 ml) and DMF (50 ml), and 10% palladium on carbon (1 g) was added thereto. The mixture was hydrogenated at 50° C. After completion of reaction, the catalyst was filtered off and the filtrate was evaporated under reduced pressure. The resultant residue was purified by silica-gel column chromatography (eluent:ethyl acetate:methanol=100:2) to give 1-(3-hydroxybenzoyl)-6-[4-(3,4-dimethoxybenzoyl)-1-piperazinyl]-3,4-dihydrocarbostyril (4.0 g).

m.p. 114° to 134° C. (decomposed)

yellow powder

NMR (CDCl$_3$) δ: 2.52-2.85 (m, 2H), 2.85-3.15 (m, 2H), 2.90-3.30 (m, 4H), 3.60-4.10 (m, 4H), 3.82 (s, 3H), 3.88 (s, 3H), 6.65-7.40 (m, 10H)

IR $\nu_{max}^{KBr}$: 3430, 1725, 1630, 1610, 1585, 1505, 1435, 1290, 1270, 1230, 1020 cm$^{-1}$

Example 30

1-(4-Hydroxybenzoyl)-6-[4-(3,4-dimethoxybenzoyl)-1-piperazinyl]-3,4-dihyrocarbostyril (9 g) was suspended in DMF (90 ml). To the suspension were added potassium carbonate (2.82 g) and benzyl monochloroacetate (3.81 g) and the mixture was stirred at room temperature over night. After completion of reaction, the reaciton mixture was poured into water and extracted with dichloromethane. The extract was washed successively with water and saturated saline solution, dried over magnesium sulfate and evaporated under reduced pressure. The residue was purified by silica-gel column chromatography [eluent:dichloromethane:methanol=100:0 to 100:5] to give 1-(4-benzyloxycarbonylmethoxybenzoyl)-6-[4-(3,4-dimethoxybenzoyl)-1-piperazinyl]-3,4-dihydroxycarbostyril (4.0 g).

NMR (CDCl$_3$) δ: 2.60–2.90 (m, 2H), 2.90–3.30 (m, 6H), 3.60–4.00 (m, 4H), 3.90 (s, 6H), 4.70 (s, 2H), 5.21 (s, 2H), 6.70–7.10 (m, 8H), 7.34 (s, 5H), 7.82 (d, 2H, J=9Hz)

EXAMPLE 31

To a solution of 1-(4-benzyloxycarbonylmethoxybenzoyl)-6-[4-(3,4-dimethoxybenzoyl)-1-piperazinyl]-3,4-dihydrocarbostyril (4 g) in a mixture of DMF (30 ml) and ethanol (30 ml) was added 10% palladium on carbon (500 mg) and the mixture was hydrogenated at room temperature and atmospheric pressure. After completion of reaction, the catalyst was filtered off and the filtrate was evaporated under reduced pressure. The residue was dissolved in dichloromethane. The solution was washed with water, dried and evaporated under reduced pressure. The resultant residue was purified by silica-gel column chromatography (eluent:dichloromethane:methanol=100:2 to 1:1) to give 1-(4-carboxymethoxybenzoyl)-6-[4-(3,4-dimethoxybenzoyl)-1-piperazinyl]-3,4-dihydrocarbostyril (3.1 g).

yellow crystals

NMR (CDCl$_3$) δ: 2.68–2.81 (m, 2H), 2,90–3.30 (m, 6H), 3.60–3.90 (m, 4H), 3.88 (s, 3H), 3.91 (s, 3H), 4.63 (brs, 2H), 6.60–7.05 (m, 8H), 7.82 (d, 2H, J=9Hz)

In an analogous manner as Example 31, the same compound as that obtained in Example 25 mentioned before was prepared using appropriate starting materials.

EXAMPLE 32

1-(4-Hydroxybenzoyl)-6-[4-(3,4-dimethoxybenzoyl)-1-priperazinyl]-3,4-dihydrocarbostyril (900 mg), N, N-dimethylmethyleneammonium iodide (360 mg) and potassium carbonate (360 mg) were suspended in dichloromethane (30 ml) and the suspension was stirred at room temperature for 4 hours. Then, additional dimethylmethyleneammonium iodide (180 mg) and potassium carbonate (180 mg) were added thereto and the mixture was stirred at room temperature over night. After completion of reaction, crystals which formed were filtered off and dichloromethane was removed under reduced pressure. The resulting residue was purified by silica-gel column chromatography (eluent:dichloromethane:methanol=100:1 to 100:2) to give 1-(4-hydroxy-3-dimethylaminomethylbenzoyl)-6-[4-(3,4-dimethoxybenzoyl)-1-piperazinyl]-3,4dihydrocarbostyril (0.8 g).

yellow crystals

NMR (CDCl$_3$) δ: 2.34 (s, 6H), 2.60–2.90 (m, 2H), 2.90–3 30 (m, 6H), 3.70 (s, 2H), 3.65–3.90 (m, 4H), 3.90 (s, 6H), 6.65–7.11 (m, 7H), 7.65 (dd, 1H, J=2Hz, 8Hz), 7.78 (s, 1H)

EXAMPLE 33

To a solution of 1-(3,5-dihydroxybenzoyl)-6-[4-(3,4-dimethoxybenzoyl)-1-piperazinyl]-3,4-dihydrocarbostyril (30 mg) in dichloromethane (1 ml) were added triethylamine (24 μl) and acetic anhydride (16 μl) and the mixture was stirred at room temperature for 1.5 hours. After completion of reaciton, the mixture was purified by preparative thin layer chromatography to give 1-(3,5-diacetoxybenzoyl)-6-[4-(3,4-dimethoxybenzoyl)-1-piperazinyl]-3,4-dihydrocarbostyril (26 mg).

yellow crystals

NMR (CDCl$_3$) δ: 2.28 (s, 6H), 2.50–2.90 (m, 2H), 2.82–3.30 (m, 6H), 3.60–4.00 (m, 4H), 3.90 (s, 6H), 6.65–7.50 (m, 9H)

In an analogous manner as Example 33, the same compound as that obtained in Example 4 mentioned before was prepared using appropriate starting materials.

EXAMPLE 34

To a suspension of 6-[4-(3,4-dimethoxybenzoyl)-1-piperazinyl]-3,4-dihydrocarbostyril (7.5 g) in DMF (75 ml) was added sodium hydride (60% in oil, 0.83 g) and the mixture was stirred at 80° to 90° C. for one hour. After cooling to room temperature, the mixture was cooled to −10° C. and a solution of benzoic anhydride (5.06 g) in tetrahydrofuran (20 ml) was added dropwise thereto with stirring. After completion of addition, the mixture was stirred at the same temperature for one hour, poured into water and extracted with ethyl acetate. The extract was washed successively with water and saturated saline solution, dried and evaporated under reduced pressure. The resultant residue was purified by silica-gel column chromatography [eluent:dichloromethane:methanol=100:0 to 100:1.5] to give 1-benzoyl-6-[4-(3,4-dimethoxybenzoyl)-1-piperazinyl]-3,4-dihydrocarbostyril (4.0 g).

yellow crystals

NMR (CDCl$_3$) δ: 2.62–2.93 (m, 2H), 2.93–3.50 (m, 6H), 3.70–4.00 (m, 4H), 3.90 (s. 6H), 6.70–7.90 (m, 11H),

In an analogous manner as Example 34, the same compounds as those obtained in Examples 1, 2 and 6 to 25 mentioned before were prepared using appropriate starting materials.

Preparation Example 1

| | |
|---|---|
| 1-(4-Hydroxybenzoyl)-6-[4-(3,4-dimethoxybenzoyl)-1-piperazinyl]-3,4-dihydrocarbostyril | 5 mg |
| Starch | 132 mg |
| Magnesium stearate | 18 mg |
| Lactose | 45 mg |
| Total | 200 mg |

Tablets each having the above composition were prepared in a conventional manner.

Preparation Example 2

| | |
|---|---|
| 1-(3-Hydroxybenzoyl)-6-[4-(3,4-dimethoxybenzoyl)-1-piperazinyl]-3,4-dihydrocarbostyril | 10 mg |
| Starch | 127 mg |
| Magnesium stearate | 18 mg |

-continued

| | |
|---|---|
| Lactose | 45 mg |
| Total | 200 mg |

Tablets each having the above composition were prepared in a concentional manner.

Preparation Example 3

| | |
|---|---|
| Sodium [6-[4-(3,4-dimethoxybenzoyl)-1-piperazinyl]-1,2,3,4-tetrahydro-2-oxoquinoline-1-carbonyl]-4-phenolate | 500 mg |
| Sodium chloride | 0.9 g |
| Distilled water for injection | 100 ml |

The above sodium chloride was dissolved in the distilled water at 80° C. while stirring. The resulting solution was cooled to 40° C. and the compound of the invention was dissolved therein. Then, distilled water for injection was added to adjust the volume to final one. The mixture was filtered using a suitable filter paper to sterilize and then filled in an ampoule of 1 ml, thus forming preparation for injection.

Preparation Example 4

| | |
|---|---|
| 1-(3-Carboxybenzoyl)-6-[4-(3,4-dimethoxybenzoyl)-1-piperazinyl]-3,4-dihydrocarbostyril | 5 mg |
| Starch | 132 mg |
| Magnesium stearate | 18 mg |
| Lactose | 45 mg |
| Total | 200 mg |

Tablets each having the above compostion were prepared in a conventional manner.

Pharmacological Tests

Pharmacological activity of the compounds of this invention was determined as described below.

[Pharmacological Test A]

Experiments were carried out on adult mongrel dogs of either sex. The papillary muscle preparations were obtained from dogs weighing 8–13 kg, anesthetized with pentobarbital sodium (30 mg/kg i.v.), given heparin sodium (1,000 U/kg i.v.) and exsanguinated. The preparation was essetially the anterior papillary muscle excised together with the ventricular septum and was set up in cold Tyrode's solution. The preparation was placed in a glass water jacket maintained at about 38° C. and cross-circulated through the cannulated anterior septal artery with blood from a donor dog at a constatn pressure of 100 mmHg. Dogs used as donors were 18–27 kg in body weight and were anesthetized with pentobarbital sodium (30 mg/kg i.v.). Heparin sodium was given at a dose of 1,000 U/kg i.v. The papillary muscle was driven with rectangular pulse about 1.5 times the threshold voltage (0.5–3 V) and 5 msec duration at a fixed rate of 120 beats/min. Through bipolar pacing electrodes. Tension developed by the papillary muscle was measured with a strain-guage transducer. The muscle was loaded with a weight of about 1.5 g. Blood flow through the anterior septal artery was measured by an electro-magnetic flow meter. Recording of developed tension and blood flow was made on charts with an ink-writing rectigraph. Details of the preparation have been described by Endoh and Hashimoto (*Am. J. Physiol.* 218, 1459–1463, 1970). The compounds in volumes of 10–30 μl were injected intra-arterially in 4 sec. The inotropic effects of the compounds are expressed as a percentage of the developed tension before the injection of the compounds. The effects of the compounds on blood flow are expressed as difference (ml/min.) between the values before and after the injection of the compounds. The results obtained are shown in Table 2 below.

Test compounds 1. 1-Acetyl-6-[4-(3,4-dimethoxybenzoyl)-1-piperazinyl]-3,4-dihydrocarbostyril
2. 1-(3-Carboxybenzoyl)-6-[4-(3,4-dimethoxy benzoyl)-1-piperazinyl]-3,4-dihydrocarbostyril
3. Sodium [6-[4-(3,4-dimethoxybenzoyl)-1-piperazinyl]-1,2,3,4-tetrahydro-2-oxoquinoline-1-carbonyl]-4-phenolate
4. 1-(3-Hydroxybenzoyl)-6-[4-(3,4-dimethoxybenzoyl)-1-piperazinyl]-3,4-dihydrocarbostyril
5. 1-(4-Carboxybenzoyl)-6-[4-(3,4-dimethoxybenzoyl)-1-piperazinyl]-3,4-dihydrocarbostyril
6. 1-Ethoxycarbonyl-6-[4-(3,4-dimethoxybenzoyl)-1-piperazinyl]-3,4-dihydrocarbostyril
7. 1-Benzoyl-6-[4-(3,4-dimthoxybenzoyl)-1-piperazinyl]-3,4-dihydrocarbostyril
8. 1-(2,4-Dihydroxybenzoyl)-6-[4-(3,4-dimethoxybenzoyl)-1-piperazinyl]-3,4-dihydrocarbostyril
9. 1-(4-Aminobenzoyl)-6-[4-(3,4-dimethoxybenzoyl)-1-piperazinyl]-3,4-dihydrocarbostyril
10. Amrinone* (reference compound)

*3-Amino-5-(4-pyridyl)-2(1H)-pyridinone

TABLE 2

| Test Compound | Dose (μmole) | % Change in Contraction of Papillary Muscle | Change in Rate of Coronary Blood Flow (ml/min.) |
|---|---|---|---|
| 1 | 1 | 20 | 2.0 |
| 2 | 3 | 44 | 2.0 |
| 3 | 3 | 20 | 1.5 |
| 4 | 3 | 14 | 2.0 |
| 5 | 1 | 8 | 1.0 |
| 10 | 1 | 27 | — |

[Pharmacological Test B]

Male and female mongrel adult dogs weighing 9–15 kg were used. Each dog was anesthetized with pentobarbital sodium, 30 mg/kg i.v., followed by continuous intravenous injection of pentobarbital sodium, 4 mg/kg/hr., to maintain a constant depth of anesthesia. Artificial ventilation is conducted using a respirator under the conditions: respiratory rate, 18/min.; inspiration volume, 20 ml/kg. Then, thoractomy was performed. The left ventricular contractile force was determined through an arch-shaped strain gauge attached to the outer wall of the left ventricle. Systemic blood pressure was measured through a pressure transducer with a polyethylene tube inserted into the left femoral artery. All parameters were recorded on an ink-writing recorder. The drug was administered through a catheter inserted into the femoral vein. The inotropic effect of the test compound was investigated 1, 5, 10, 30 and 60 min. after administration and expressed as a % change against pretreatment tension. The test results are shown in Table 3.

TABLE 3

| Test Compound | Dose (mg/Kg) | % Change in Contraction of left Ventricular | | | | |
|---|---|---|---|---|---|---|
| | | 1 min. | 5 min. | 10 min. | 30 min. | 60 min. |
| 4 | 3 | 52 | 59 | 48 | 39 | 26 |
| 6 | 3 | 40 | 24 | 14 | 14 | 14 |
| 7 | 10 | 58 | 48 | 37 | 20 | 14 |
| 8 | 10 | 69 | 50 | 31 | 6 | — |
| 9 | 10 | 20 | 41 | 28 | 27 | 19 |
| 10 | 1 | 42 | 31 | 17 | −2.5 | |

What is claimed is:

1. A carbostyril compound of the formula (I):

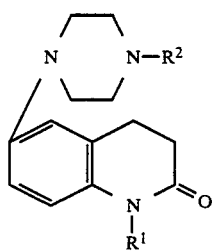

wherein $R^1$ is a lower alkanoyl group, a lower alkoxycarbonyl group, a lower alkoxycarbonyl-lower alkyl group, a phenyl-lower alkyl group which has, on the phenyl ring thereof, 1 to 3 substituents selected from among lower alkanoyloxy and hydroxy groups, a benzoyl group which may optionally be substituted, on the phenyl ring thereof, withn 1 to 3 substituents selected from the group consisting of nitro, unsubstituted or lower alkyl-substituted amino, phenyl-lower alkoxy, hydroxy, carboxy, phenyl-lower alkoxycarbonyl-lower alkoxy, lower alkanoyloxy, carboxy-lower alkoxy and lower alkyl-substituted amino-lower alkyl, or a naphthoyl group, $R^2$ is a benzoyl group which may optionally have, on the phenyl ring thereof, 1 or 2 lower alkoxy groups, and its pharmaceutically acceptable salt.

2. A carbostyril compound or its pharmaceutically acceptable salt as claimed in claim 1, wherein $R^2$ is a benzoyl group which is substituted with 1 or 2 of a $(C_{1-6})$alkoxy group.

3. A carbostyril compound or its pharmaceutically acceptable salt as claimed in claim 2, wherein $R^1$ is a benzoyl group which may optionally be substituted, on the phenyl ring thereof, with 1 to 3 substituents selected from the group consisting of nitro, unsubstituted or $(C_{1-6})$alkyl-substituted amino, phenyl-$(C_{1-6})$alkoxy, hydroxy, carboxy, phenyl-$(C_{1-6})$alkoxycarbonyl-$(C_{1-6})$alkoxy, $(C_{1-6})$alkanoyloxy, carboxy-$(C_{1-6})$alkoxy, and $(C_{1-6})$alkylsubstituted amino-$(C_{1-6})$alkyl 4. A carbostyril compound or its pharmaceutically acceptable salt as claimed in claim 2, wherein $R^1$ is a $(C_{1-6})$alkanoyl group.

5. A carbostyril compound or its pharmaceutically acceptable salt as claimed in claim 2, wherein $R^1$ is a $(C_{1-6})$alkoxycarbonyl group, a $(C_{1-6})$alkoxycarbonyl-$(C_{1-6})$alkyl group, a phenyl-$(C_{1-6})$alkyl group which has, on the phenyl ring thereof, 1 to 3 substitutent selected from among $(C_{1-6})$alkanoyloxy and hydroxy groups, or a naphthoyl group.

6. A carbostyril compound or its pharmaceutically acceptable salt as claimed in claim 3, wherein $R^1$ is a benzoyl group which is substituted, on the phenyl ring thereof, with 1 to 3 substituents selected from the group consisting of hydroxy, carboxy, unsubstituted or $(C_{1-6})$alkyl-substituted amino, carboxy-$(C_{1-6})$alkoxy, and $(C_{1-6})$alkyl-substituted amino-$(C_{1-6})$alkyl.

7. A carbostyril compound or its pharmaceutically acceptable salt as claimed in claim 3, wherein $R^1$ is an unsubstituted benzoyl group.

8. A carbostyril compound or its pharmaceutically acceptable salt as claimed in claim 6, wherein $R^1$ is a benzoyl group which is substituted, on the phenyl ring thereof, 1 to 2 substituents selected form the group consisting of unsubstituted or $(C_{1-6})$alkyl-substituted amino, hydroxy, and carboxy-$(C_{1-6})$alkoxy.

9. A carbostyril compound or its pharmaceutically acceptable salt as claimed in claim 8, wherein $R^2$ is a 3,4-di($C_{1-6}$)alkoxybenzoyl group.

10. A carbostyril compound or its pharmaceutically acceptable salt as claimed in claim 9, wherein $R^1$ is a benzoyl group which is substituted, on the phenyl ring thereof, with one substituent selected form the group consisting of unsubstituted or $(C_{1-6})$alkyl-substituted amino, and hydroxy.

11. 1-(4-Aminobenzoyl)-6-[4-(3,4-dimethoxybenzoyl)-1-piperazinyl]-3,4-dihydrocarbostyril according to claim 10.

12. 1-(4-Hydroxybenzoyl)-6-[4-(3,4-dimethoxybenzoyl)-1-piperazinyl]-3,4-dihydrocarbostyril according to claim 10.

13. 1-Benzxoyl-6-[4-(3,4-dimethoxybenzxoyl)-1-piperazinyl]-3,4-dihydrocarbostyril according to claim 7.

14. 1-(4-Hydroxy-3-dimethylaminomethylbenzxoyl)-6-[4-(3,4-dimethoxybenzoyl)-1-piperazinyl]-3,4-dihydrocarbostyril according to claim 9.

15. 1-(3-Hydroxy-5-carboxymethoxybenzoyl)-6-[4-(3,4-dimethoxybenzoyl)-1-piperazinyl]-3,4-dihydrocarbostyril according to claim 9.

16. A carbostyril compound or its pharmaceutically acceptable salt as claimed in claim 5, wherein $R^1$ is a $(C_1-C_6)$ alkoxycarbonyl group.

17. A carbostyril compound of the formula (I):

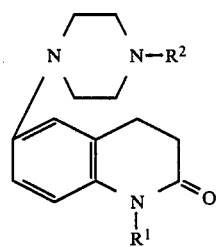

wherein $R^1$ is a lower alkanoyl group, a lower alkoxycarbonyl group, a benzoyl group which may optionally be substituted, on the phenyl ring thereof, with 1 to 2 substituents selected from the group consisting of unsubstituted amino, hydroxy, and carboxy, $R^2$ is a benzoyl group which may optionally have, on the phenyl ring thereof, 1 or 2 of a lower alkoxy group, and its pharmaceutically acceptable salt.

18. A carbostyril compound or its pharmaceutically acceptable salt as claimed in claim 17, wherein $R^1$ is a benzoyl group which is substituted, on the phenyl ring thereof, 1 to 2 substituents selected from the group consisting of unsubstituted amino, hydroxy, and carboxy.

19. A carbostyril compound or its pharmaceutically acceptable salt as claimed in claim 18, wherein $R^1$ is a benzoyl group which is substituted, on the phenyl ring thereof, with one substituent selected from the group consisting of unsubstituted amino and hydroxy.

20. A cardiotonic composition comprising a cardiotonically effective amount of a compound of the formula (I):

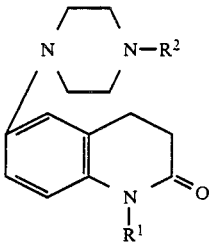

wherein $R^1$ is a lower alkanoyl group, a lower alkoxycarbonyl group, a lower alkoxycarbonyl-lower alkyl group, a phenyl-lower alkyl group which has, on the phenyl ring thereof, 1 to 3 substituents selected from among lower alkanoyloxy and hydroxy groups, a benzoyl group which may optionally be substituted, on the phenyl ring thereof, with 1 to 3 substituents selected from the group consisting of nitro, unsubstituted or lower alkyl-substituted amino, phenyl-lower alkoxy, hydroxy, carboxy, phenyl-lower alkoxycarbonyl-lower alkoxy, lower alkanoyloxy, carboxyl-lower alkoxy, and lower alkyl-substituted amino-lower alkyl, or a naphthoyl group, $R^2$ is a benzoyl group which may optionally have, on the phenyl ring thereof, 1 or 2 lower alkoxy groups, and its pharmaceutically acceptable salt.

* * * * *